United States Patent [19]

Santroch et al.

[11] 4,132,709

[45] Jan. 2, 1979

[54] [2]BENZOPYRANO[4,3-c]PYRIDINE DERIVATIVES AND PROCESS THEREFOR

[75] Inventors: George Santroch, Montreal; Leslie G. Humber, Dollard des Ormeaux, both of Canada

[73] Assignee: Ayerst, McKenna & Harrison, Ltd., Montreal, Canada

[21] Appl. No.: 752,656

[22] Filed: Dec. 20, 1976

[51] Int. Cl.$^2$ .......................................... C07D 491/04
[52] U.S. Cl. .................................... 546/89; 424/256; 546/215; 546/216
[58] Field of Search .................... 260/293.55; 424/256

[56] References Cited

U.S. PATENT DOCUMENTS 3,522,260  7/1970  Shulgin ..................... 260/293.55

Primary Examiner—Natalie Trousof
Assistant Examiner—Richard A. Schwartz
Attorney, Agent, or Firm—Stephen Venetianer

[57] ABSTRACT

[2]Benzopyrano[4,3-c]pyridine derivatives characterized by having a 2,3,4,4a,6,10b-hexahydro-1H-[2]benzopyrano[4,3-c]pyridine nucleus are disclosed. The nucleus can be optionally further substituted at positions 2,6 and on the aromatic ring. The derivatives are useful diuretic, anorexic, antidepressant, anticonvulstant and antihypertensive agents. Methods for the preparation and use of these derivatives also are disclosed.

24 Claims, No Drawings

[2]BENZOPYRANO[4,3-C]PYRIDINE DERIVATIVES AND PROCESS THEREFOR

BACKGROUND OF THE INVENTION

1. Field of the Invention

This invention relates to novel [2]benzopyrano[4,3-c]-pyridine derivatives, to processes for their preparation, to methods for using the derivatives and to pharmaceutically acceptable compositions of said derivatives.

More specifically, the present invention relates to novel 2,3,4,4a,6,10b-hexahydro-1H-[2]benzopyrano[4,3-c]pyridine derivatives possessing valuable pharmacologic properties. For example, these derivatives are useful diuretic, anoretic, antidepressant, anticonvulsant and antihypertensive agents at dosages which do not elicit undesirable side effects. The combination of these pharmacologic properties with a low order of toxicity render the [2]benzopyrano[4,3-c]pyridine derivatives of the invention therapeutically useful.

2. Description of the Prior Art

A number of reports dealing with benzopyrano[4,3-c]-pyridines are available. For example, the [1]benzopyrano[4,3-c]pyridine ring system is described by H. G. Pars et al., J. Amer. Chem. Soc., 88, 3664 (1966). The latter ring system is readily distinguished from the ring system of the present invention by having the oxygen function at a different position in the benzopyrano[4,3-c]pyridine nucleus. In addition, the compounds of this invention are prepared by a novel and useful process. Furthermore, the compounds of the present invention are distinguished from the compounds of the prior art by their unique pharmacological properties.

SUMMARY OF THE INVENTION

The compounds of this invention are represented by formula I

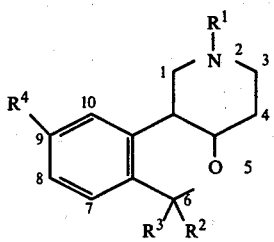

in which $R^1$ is hydrogen, lower alkyl, lower alkenyl, phenyl(lower)alkyl, lower cycloalkyl(lower)alkyl, aminoiminomethyl, cyano, amino(lower)alkyl, lower alkylamino(lower)alkyl or di(lower)alkylamino(lower)alkyl; $R^2$ is hydrogen or lower alkyl; $R^3$ is hydrogen, lower alkyl or phenyl; and $R^4$ is hydrogen, lower alkoxy or hydroxy.

Also included are the therapeutically acceptable acid addition salts of the compounds of formula I.

The novel [2]benzopyrano[4,3-c]pyridine derivatives of formula I are prepared by condensing a compound of formula II

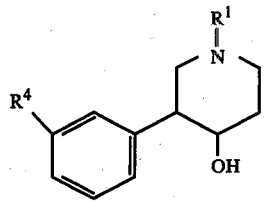

in which $R^1$ is lower alkyl and $R^4$ is hydrogen or lower alkoxy with a carbonyl compound of formula III

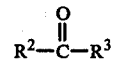

in which $R^2$ and $R^3$ are as defined herein in the presence of an acid catalyst to obtain the corresponding compound of formula I in which $R^1$ is lower alkyl, $R^2$ and $R^3$ are as defined herein and $R^4$ is hydrogen or lower alkoxy; followed when it is desired to prepare other compounds of formula I by transformation of one of the latter compounds of formula I to one of the other compounds of formula I by methods described herein.

More specifically, said transformation comprises:

reacting said compound of formula I in which $R^1$ is methyl, $R^2$ and $R^3$ are as defined herein and $R^4$ is hydrogen or lower alkoxy with cyanogen bromide to obtain the corresponding compound of formula I in which $R^1$ is cyano and $R^2$, $R^3$ and $R^4$ are as defined immediately above; or reducing said last-named compound of formula I with a complex metal hydride to obtain the corresponding compound of formula I in which $R^1$ is hydrogen and $R^2$, $R^3$ and $R^4$ are as defined immediately above; or reacting said compound of formula I in which $R^1$ is methyl and $R^2$, $R^3$ and $R^4$ are as defined immediately above with phenyl chloroformate followed by heating with powdered sodium or potassium hydroxide to obtain the corresponding compound of formula I in which $R^1$ is hydrogen and $R^2$, $R^3$ and $R^4$ are as defined immediately above; or reacting said last-named compound of formula I with S-methylpseudothiourea to obtain the corresponding compound of formula I in which $R^1$ is aminoiminomethyl and $R^2$, $R^3$ and $R^4$ are as defined immediately above; or reacting said compound of formula I in which $R^1$ is hydrogen and $R^2$, $R^3$ and $R^4$ are as defined immediately above with a lower cycloalkylcarbonyl halide, lower alkanoyl halide, lower cycloalkyl(lower)alkanoyl halide, phenyl(lower)alkanoyl halide or benzoyl halide wherein the halide is selected from chlorine, bromine or iodine followed by reduction of the corresponding amide, so obtained, with a complex metal hydride to obtain the corresponding compound of formula I in which $R^1$ is lower alkyl, lower cycloalkyl(lower)alkyl or phenyl(lower)alkyl and $R^2$, $R^3$ and $R^4$ are as defined immediately above; or reacting said compound of formula I in which $R^1$ is hydrogen and $R^2$, $R^3$ and $R^4$ are as defined immediately above with a lower alkyl halide, lower cycloalkyl(lower)alkyl halide or lower alkenyl halide wherein the halide is bromide, chloride or iodide to obtain the corresponding compound of formula I in which $R^1$ is lower alkyl, lower cycloalkyl(lower)alkyl or lower alkenyl and $R^2$, $R^3$ and $R^4$ are as defined immediately above; or reacting said compound of formula I in which $R^1$ is hydrogen and $R^2$, $R^3$ and $R^4$ are as defined immediately above with a proton acceptor followed by a di(lower)alkylamino(lower)alkyl chloride, bromide or iodide to obtain the corresponding compound of formula I in which $R^1$ is di(lower)alkylamino(lower)alkyl and $R^2$, $R^3$ and $R^4$ are as defined immediately above; or reacting said compound of formula I in which $R^1$ is hydrogen and $R^2$, $R^3$ and $R^4$ are as defined immediately above with an ω-halo-alkanoyl halide wherein each of the halogen atoms is chlorine, bromine or iodine in the presence of an organic proton acceptor to obtain the corresponding ω-halo(lower)alkanoyl intermediate, reacting the latter intermediate with ammonia, lower alkylamine or di(lower)alkylamine in the presence of an inorganic proton acceptor to obtain the corresponding amino, lower alkylamino or di(lower)alkylamino alkanoyl intermediate and reducing the latter intermediate with a complex metal hydride to obtain the corresponding compound of formula I in which $R^1$ is amino(lower)alkyl, lower alkylamino(lower)alkyl or di(lower)alkylamino(lower)alkyl, $R^2$ and $R^3$ are as defined herein and $R^4$ is hydrogen or lower alkoxy; or heating said compound of formula I in which $R^1$, $R^2$ and $R^3$ are as defined herein and $R^4$ is lower alkoxy with pyridine hydrochloride to obtain the corresponding compound of formula I in which $R^1$, $R^2$ and $R^3$ are as defined herein and $R^4$ is hydroxy.

Another aspect of this invention involves a method for increasing the excretion of urine (diuresis) as well as suppression of appetite in a mammal which comprises administering to said mammal an effective amount of a compound of formula I, or a therapeutically acceptable salt thereof.

Still another aspect of this invention involves a method of treating depression, convulsions and hypertension in a mammal which comprises administering to said mammal an effective amount of a compound of formula I, or a therapeutically acceptable salt thereof.

Still another aspect of this invention involves a pharmaceutical composition comprising a compound of formula I, or a therapeutically acceptable salt thereof, and a pharmaceutically acceptable carrier.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "lower cycloalkyl" as used herein contemplates saturated cyclic hydrocarbon radicals containing form three to six carbon atoms and includes cyclopropyl, cyclobutyl, cyclohexyl and the like.

The term "lower alkoxy" as used herein contemplates straight chain alkoxy radicals containing from one to six carbon atoms and branched chain alkoxy radicals containing from three to four carbon atoms and includes methoxy, ethoxy, isopropoxy, butoxy, hexanoxy and the like.

The term "lower alkanoyl" as used herein contemplates both straight and branched chain alkanoyl radicals containing from two to six carbon atoms and a branched chain alkanoyl radical containing four carbon atoms and includes acetyl, propionyl, isobutyryl, hexanoyl and the like.

The term "lower alkenyl" as used herein contemplates both straight and branched chain alkenyl radicals containing from two to six carbon atoms and includes ethenyl, 2-methyl-2-propenyl, 2-ethyl-3-butenyl, 4-hexenyl and the like.

The term "phenyl(lower)alkyl" as used herein contemplates a phenylalkyl radical in which the alkyl portion thereof contains from one to six carbon atoms and includes benzyl, 2-phenylethyl, 2-methyl-3-phenylpropyl, 5-phenylpentyl and the like.

The term "lower cycloalkyl(lower)alkyl" as used herein contemplates a lower cycloalkyl(lower)alkyl radical in which the alkyl portion thereof is a straight chain containing from one to six carbon atoms or a branched chain containing from two to four carbon atoms and includes cyclopropylmethyl, 5-cyclobutylpentyl, 1-methyl-3-cyclopentylpropyl, 2-ethyl-2-cyclohexylethyl and the like. Thus, the lower cycloalkyl(lower)alkyl can contain 4 to 12 carbon atoms.

The term "lower alkanol" as used herein contemplates both straight and branched alkanols containing from one to four carbon atoms and includes methanol, isopropanol, butanol and the like.

The term "lower alkanoic acid" as used herein contemplates both straight and branched chain alkanoic acids containing from two to six carbon atoms and includes acetic acid, butanoic acid, hexanoic acid and the like.

Where the term "(lower)alkyl" is used in connection with the alkylene portion of amino(lower)alkyl, lower alkylamino(lower)alkyl and di(lower)alkylamino(lower)alkyl, it contemplates a divalent organic radical derived from a straight chain aliphatic hydrocarbon containing from one to six carbon atoms or a branched chain aliphatic hydrocarbon containing from two to four carbon atoms and includes methylene, 2-methylpropylene, ethylene, hexylene and the like.

The term "proton acceptor" as used herein contemplates the organic bases, or amines for instance, triethylamine, pyridine, N-ethylmorpholine, 1,5-diazabicyclo[3.4.0]nonene-5 and the like, as well as the inorganic bases, preferably the alkali metal hydroxides, carbonates, hydrides, amides and alkoxides, for example, sodium ethoxide, sodium hydroxide, potassium hydroxide, potassium carbonate, sodium methoxide, sodium hydride and the like.

The term "complex metal hydride" contemplates metal hydrides and includes lithium aluminum hydride, lithium aluminum hydride-aluminum chloride, aluminum hydride-aluminum chloride, diborane, sodium borohydride-aluminum chloride and the like.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, ether (i.e., diethyl ether) or an ethanol-ether mixture. These salts, when administered to a mammal, possess the same pharmacologic activities as the corresponding bases. For many purposes it is preferable to administer the salts rather than the base compounds. Suitable acids to form these salts include, for example the common mineral acids, hydrohalic, sulfuric, or phosphoric, as well as the organic acids, formic, acetic, maleic, malic, citric, or tartaric acid, or acids which are sparingly soluble in body fluids and which impart slow-release properties to their respective salts such as pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I which result from asymmetric centers, contained therein.

Individual optical isomers, which might be separated by fractional crystallization of the diastereoisomeric salts thereof, for instance, salts with d- or l-tartaric acid or D-(+)-α-bromocamphor sulfonic acid, are also included.

The compounds of this invention of formula I or a therapeutically acceptable salt thereof are useful antihypertensive agents in a mammal upon oral or parenteral administration.

The antihypertensive effect of the compounds of formula I and their acid addition salts is demonstrated in standard pharmacological tests. For example, in tests conducted in the spontaneously hypertensive rat (SHR), such as described by R. Tabei et al., Clin. Pharmacol. Therap. II, 269 (1970) or I. Vavra et al., Can. J. Physiol. Pharmacol., 51, 727 (1973). More specifically exemplified, a testing method such as described in the latter publication shows that the preferred compounds (4a,10b-trans)-2,3,4,4a,6,10b-hexahydro-2-methyl-1H-[2]-benzopyrano[4,3-c]pyridine (Example 4), (4a,10b-trans)-2,3,4,4a,6,10b-hexahydro-1H-[2]benzopyrano[4,3-c]pyridine (Example 9) and (4a,10b-trans)-2,3,4,4a,6,10b-hexahydro-2-ethyl-1H-[2]-benzopyrano[4,3-c]pyridine (Example 12) cause a notable blood pressure decrease in the SHR at about four hours after a dose of 5 to 25 mg per kilogram of body weight perorally.

When the compounds of formula I of this invention are used as antihypertensive agents in mammals e.g. rats, dogs and mice, they are used alone or in combination with pharmacologically acceptable carriers, the proportion of which is determined by the solubility and chemical nature of the compound, chosen route of administration and standard biological practice. For example, they are administered orally in solid form i.e. capsule or tablet. They may also be administered orally in the form of suspensions or solutions or they may be injected parenterally. For parenteral administration they may be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets may be uncoated or they may be coated by known techniques so as to delay disintegration and absorption in the gastrointestinal tract and thereby provide a sustained action over a long period.

The aqueous suspensions of the invention contain the active ingredient in admixture with one or more non-toxic pharmaceutical excipients known to be suitable in the manufacture of aqueous suspensions. Suitable excipients are, for example, methyl-cellulose, sodium alginate, gum acacia, lecithin and so forth. The aqueous suspensions may also contain one or more preservatives, one or more colouring agents, one or more flavouring agents and one or more sweetening agents.

Non-aqueous suspensions may be formulated by suspending the active ingredient in a vegetable oil, for example, arachic oil, olive oil, sesame oil, or coconut oil; or in a mineral oil, for example liquid paraffin. The suspension may contain a thickening agent, for example beeswax, hard paraffin or cetyl alcohol. These compositions may also contain a sweetening agent, flavouring agent and antioxidant.

The dosage of the compounds of formula I of this invention as antihypertensive agents will vary with the form of administration and the particular compound chosen. Furthermore, it will vary with the particular host as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective antihypertensive amount of the compounds usually ranges from about 1.0 mg to about 500 mg per kilogram of body weight per day, although as aforementioned variations will occur. However a dosage level that is in range of from about 10 mg to about 300 mg per kilogram of body weight per day is employed most desirably in order to achieve effective results.

The antidepressant activity of the compounds of formula I or their acid addition salts with therapeutically acceptable acids is demonstrated in standard pharmacologic tests such as, for example, the tests described by F. Hafliger and V. Burckhart in "Psychopharmacological Agents", M. Gordon, Ed., Academic Press, New York and London, 1964, pp. 75–83.

More specifically, as noted in the latter reference the antidepressant properties of a compound may be demonstrated by its capacity to antagonize the depressant effects of reserpine. Furthermore, it is well documented that reserpine in animals produces a model depression which can be used for detecting antidepressant properties. Accordingly, the compounds of the present invention antagonize reserpine effects in mice at doses ranging from about 1 to 50 mg per kilogram of body weight. The preferred compounds (4a,10b-trans)-2,3,4,4a,6,10b-hexahydro-2,6,6-trimethyl-1H-[2]benzopyrano[4,3-c]pyridine (Example 3), (4a,10b-trans)-2,3,4,4a,6,10b-hexahydro-2-methyl-1H-[2]benzopyrano[4,3-c]-pyridine (Example 4) and (4a,10b-trans)-2,3,4,4a,6,10b-hexahydro-2,6-dimethyl-1H-[2]benzopyrano[4,3-c]pyridine (Example 6) antagonize reserpine effects at a peroral dose level of 1-10 mg per kilogram of body weight.

In general, the compounds of this invention are most desirably administered at a concentration level that will generally afford effective results without causing any harmful or deleterious side effects and preferably at a level that is in the range of from about 0.1 mg to about 100 mg per kilogram of body weight per day, although as aforementioned variations will occur. Howerver, a dosage level that is in the range of from about 0.5 mg to about 50 mg per kilogram of body weight per day is most desirably employed in order to achieve effective results.

The compounds of formula I or therapeutically acceptable salts thereof are shown to be effective diuretic agents in mammals by tests conducted in rats. As example of such a test for diuretic agents in rats is described by J. R. Cummings et al., J. Pharmacol. Exp. Ther., 414, 128(1960). In this test, the urine of the rats is collected for five hours, during which time food and water are withdrawn. Urine volumes as well as sodium potassium and chloride ion concentrations are determined. The compounds of this invention exhibit a dose response dependency when they are orally administered in dosages ranging from 5 to 100 mg per kilogram of body weight. For instance, the following compound of this invention, (4a, 10b-cis)-2,3,4,4a,6,10b-hexahydro-9-methoxy-2,6,6-trimethyl 1-1H-[2]benzo- pyrano[4,3-c]pyridine (Example 5), is an effective diuretic agent at an oral dose of 25 mg per kilogram of body weight.

The compounds of formula I or their acid addition salts with therapeutically acceptable acids also exhibit anorexic activity in a mammal. A suitable test for appetite suppression is described by G. A. Heise in "Animal and Clinical Pharmacologic Techniques in Drug Evaluation", Vol 1, edited by J. H. Nodine and P. E. Siegler, Year Book Medical Publishers, Inc. Chicago, 1964, pp. 279-282. Rats are trained to consume food during a four hour period in the morning. Food consumption is measured at one and four hours after p.o. administration of a standard (d-amphetamine) or the test compound and compared with the consumption of food by control rats given the vehicle only. This testing method shows that the preferred compounds (4a,10b-cis)-2,3,4,4a,6,10b-hexahydro-2,6,6-trimethyl-1H[2]-benzopyrano[4,3-c]pyridine (Example 3) and (4a,10b-cis)-2,3,4,4a,6,10b-hexahydro-9-methoxy-2,6,6-trimethyl-1H-[2]-benzopyrano[4,3-c]pyridine (Example 5) at oral doses of 10 to 25 mg per kilogram of body weight reduce food consumption in the rat.

The anticovulsant activity of the compounds of formula I or their acid addition salts with therapeutically acceptable acids is demonstrated in a modification of the Maximal Electroshock Seizure (MES) method described by F. M. Berger, Proc. Soc. Exp. Biol., 78, 277 (1951). Albino male mice weighing between 18–24 g are used. Seizures are produced by applying through corneal electrodes a current of 30 milliamps for 0.2 second. The precent of mice which are protected from the tonic phase of the seizure are recorded for each dose. Several of the preferred compounds, for example, (4a,10b-trans)-2,3,4,4a,6,10b-hexayddro-1H-[2]benzopyrano[4,3-c]pyridine-2-carbonitrile (Example 8), (4a,10b-trans)-2,3,4,4a,6,10b-hexahydro-1H[2]benzopyrano[4,3-c]-pyridine (Example 9) and (4a,10b-trans)-2,3,4,4a,6,10b-hexahydro-2-ethyl-1H-[2]benzopyrano[4,3-c]pyridine (Example 12) protects mice against MES at an i.p. dose level of 10–40 mg per kilogram of body weight.

When the compounds of formula I or a therapeutically acceptable salt thereof are used as antidepressant, diuretic, anorexic or anticonvulsant agents in a mammal, they are formulated (i.e., capsule or tablet, aqueous solutions or suspensions and non-aqueous suspensions) and administered in a similar manner as described above for their use as antihypertensive agents.

PROCESSES

Useful and practical starting materials for the preparation of the compounds of formula I are the compounds of formula II

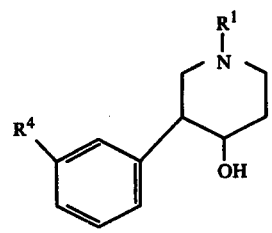

in which $R^1$ is lower alkyl and $R^4$ is hydrogen or lower alkoxy. The compounds of formula II can exist in the form of two isomers: formula IIa represents the cis isomer and formula IIb represents the trans isomer.

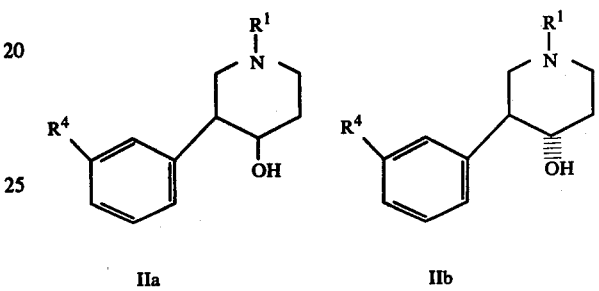

The starting materials of formula IIa and IIb are readily obtained by the reduction of the corresponding 4-piperidone of formula IV

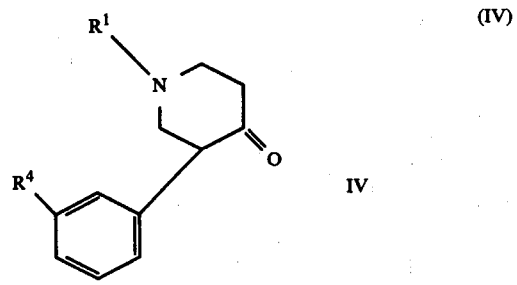

in which $R^1$ is lower alkyl and $R^4$ is hydrogen or lower alkoxy. A suitable means of reduction comprises reacting the compound of formula IV with sodium borohydride in a water-methanol solution for 15 to 120 minutes at 10° to 50° C. Careful purification of the product from the reaction, for instance by fractional crystallization and/or chromatography, yields the separate compounds of formulae IIa and IIb.

The compound of formula IV in which $R^1$ is methyl and $R^4$ is hydrogen is described by A. A. Patchett and F. F. Gianusso, J. Med. Chem., 4 385(1965). Other compounds of formula IV are prepared by using the appropriate starting materials and following the procedure described in the latter reference.

The novel [2]benzopyrano[4,3,-c]pyridines of this invention are readily and conveniently prepared by the following process:

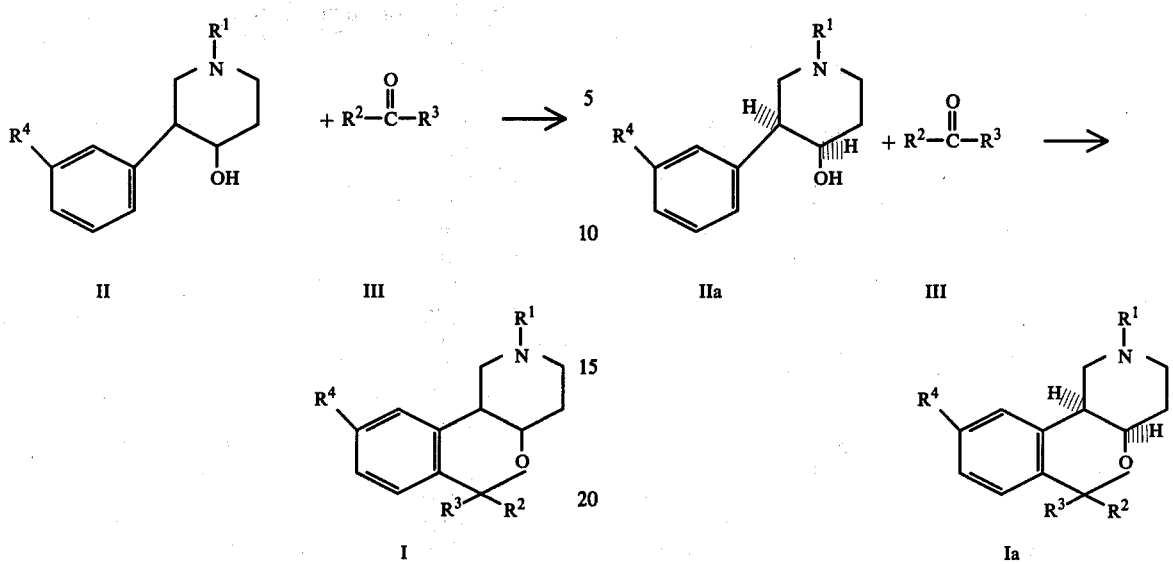

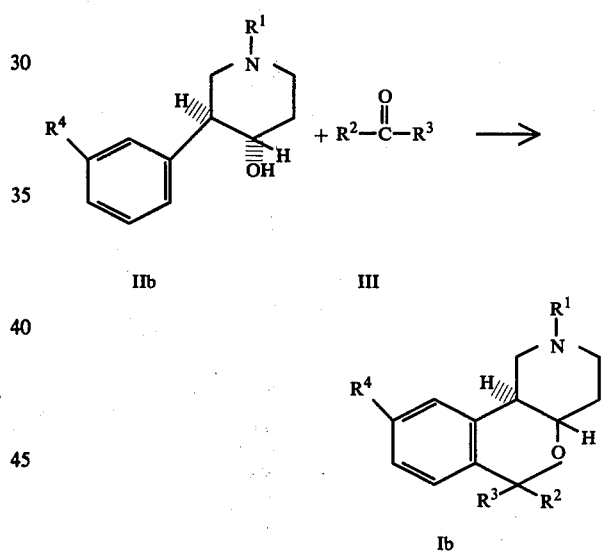

in which R¹ is lower alkyl, R² and R³ are as defined herein and R⁴ is hydrogen or lower alkoxy.

With reference to the above process, the starting material of formula II is condensed with one to five molar equivalents of a carbonyl compound of formula III in the presence of an acid catalyst to obtain the corresponding compound of formula I.

In practising the condensation (II + III → I) any solvent inert to the reaction conditions can be used. Suitable solvents include the cyclic ethers (i.e., doixane, tetrahydrofuran and the like) and the lower alkanols (i.e., methanol, ethanol and the like). Dioxane and methanol are especially convenient and practical as solvents. The acid catalysts suitable for this condensation can be selected from hydrogen bromide, hydrogen chloride, boron trifluoride etherate and the like. When R⁴ is hydrogen the preferred acid catalyst is hydrogen bromide. The amount of acid catalyst is not especially critical and may range from 5 to 100 molar equivalents. The time of the reaction can range from 0.5 to 100 hours at a temperature from −10° to 50° C. The time and temperature of a specific reaction is dependent upon the condensation rate of the particular compounds of formula II and III as well as the acid catalyst. During the condensation it is advantageous to remove the water formed. The addition of an anhydrous alkali-aluminum silicate (molecular sieves) to the reaction mixture is an effective means to remove the water.

The carbonyl compounds of formula III are ketones or aldehydes which are either known, for example, acetone, benzaldehyde, propionaldehyde and acetaldehyde or they can be prepared by known methods described in general organic chemistry textbooks. For example, a comprehensive review on the properties and preparation of such ketones and aldehydes may be found in "Rodd's Chemistry of Carbon Compounds", S. coffey, Ed. Vol. Ic, 2nd ed., Elsevier Publishing Co., Amsterdam, 1965, pp, 1-99.

The compounds of formula I can exist as two isomers depending upon which isomer of formula II is used as starting material. For instance, the cis isomer of formula IIa gives the cis isomer of formula Ia, as illustrated by the following scheme.

Correspondingly, the trans isomer of formula IIb gives the trans isomer of formula Ib and is illustrated by the following scheme.

The compounds of formula I prepared as described above can be further transformed to obtain other compounds of formula I.

For instance, the compound of formula I in which R¹ is methyl, R² and R³ are as defined herein and R⁴ is hydrogen or lower alkoxy is reacted with cyanogen bromide in an inert solvent, such as chloroform, for one to three hours at about 60° C. The solution is evaporated and water is added. The mixture is heated to reflux, cooled and purified to give the corresponding compound of formula I in which R¹ is cyano, R² and R³ are as defined herein and R⁴ is hydrogen or lower alkoxy.

Reduction of the latter compound, preferably with lithium aluminum hydride in an inert solvent such as dioxane or tetrahydroguran at about 60° to 70° C. for two to five hours, gives the corresponding compound of formula I in which R¹ is hydrogen, R² and R³ are as defined herein and R⁴ is hydrogen or lower alkoxy.

Another useful conversion of the compound of formula I in which $R^1$ is methyl, $R^2$ and $R^3$ are as defined herein and $R^4$ is hydrogen or lower alkoxy consists of reacting the latter compound with three to ten molar equivalents or phenyl chloroformate in an inert solvent (i.e., benzene, toluene and like) at about 80° to 110° C. for five to ten hours to obtain the corresponding intermediate having a phenoxycarbonyl group at position 2 of the [2]benzopyrano[4,3-c]pyridine ring system. The latter intermediate is heated with a molar excess of powdered sodium or potassium hydroxide at 100° to 150° C. for about one hour, a solution of water-ethanol is added and the solution is heated at the boiling point of the reaction mixture for one to three days to obtain the corresponding compound of formula 1 in which $R^1$ is hydrogen, $R^2$ and $R^3$ are as defined herein and $R^4$ is hydrogen or lower alkoxy.

If desired, the compound of formula I in which $R^1$ is hydrogen, $R^2$ and $R^3$ are as defined herein and $R^4$ is hydrogen or lower alkoxy is heated with S-methylpseudothiourea and potassium carbonate in an inert solvent consisting of a 1:1 mixture of water and a lower alkanol (i.e., isopropanol) at the boiling point of the reaction mixture for 20 to 30 hours. The reaction is cooled and purified to obtain the corresponding compound of formula I in which $R^1$ is aminoiminomethyl, $R^2$ and $R^3$ are as defined herein and $R^4$ is hydrogen or lower alkoxy.

Another transformation of the compound of formula I in which $R^1$ is hydrogen, $R^2$ and $R^3$ are as defined herein and $R^4$ is hydrogen or lower alkoxy comprises reacting the latter compound of formula I with a lower alkanoyl halide, lower cycloalkylcarbonyl halide, lower cycloalkyl(lower)alkanoyl halide, phenyl(lower)alkanoyl halide or benzoyl halide wherein the halide is chloride, iodide or bromide in the presence of a proton acceptor at a temperature of $-10°$ to 10° C. for one-half to two hours to obtain the corresponding intermediate having an amide function at position 2. The preferred proton acceptor is an inorganic base selected from the hydroxides or carbonates of sodium or potassium and the preferred inert solvents include methylene chloride, chloroform and the like. The intermediate amide is reduced, preferably with a complex metal hydride, for example, lithium aluminum hydride, in a solvent selected from dioxane or tetrahydrofuran at a temperature of 50° to 70° C. for about one-half to five hours, to obtain the corresponding compound of formula I in which $R^1$ is lower alkyl, lower cycloalkyl(lower)alkyl or phenyl(lower)alkyl, $R^2$ and $R^3$ are as defined herein and $R^4$ is hydrogen or lower alkoxy.

Alternatively, the compound of formula I in which $R^1$ is hydrogen is reacted with a lower alkanoic acid anhydride in the presence of a proton acceptor, for instance an organic amine selected from triethylamine, N-methylmorpholine and the like, in an inert solvent, preferably dichloroethane and the like, at a temperature of 50° C. to the boiling point of the reaction mixture for about 15 to 100 minutes to obtain the corresponding intermediate amide. Reduction of the latter amide with a complex metal hydride (i.e., lithium aluminum hydride) in the same manner as described above gives the corresponding compound of formula I in which $R^1$ is lower alkyl, $R^2$ and $R^3$ are as defined herein and $R^4$ is hydrogen or lower alkoxy.

The compound of formula I in which $R^1$ is lower alkyl, lower cycloalkyl(lower)alkyl or lower alkenyl, $R^2$ and $R^3$ are as defined herein and $R^4$ is hydrogen or lower alkoxy is conveniently prepared by reacting the corresponding compound of formula I in which $R^1$ is hydrogen with 1.1 to 2.0 molar equivalents of a lower alkyl halide, lower cycloalkyl(lower)alkyl halide or lower alkenyl halide wherein the halide is bromide, chloride or iodide and 1.1 to 2.0 molar equivalents of a proton acceptor in an inert solvent (i.e. dioxane, tetrahydrofuran and the like) at 10° to 50° C. for 30 to 60 hours. Suitable proton acceptor is an inorganic base selected from the hydroxides and carbonates of sodium or potassium.

A further conversion of the compound of formula I in which $R^1$ is hydrogen, $R^2$ and $R^3$ are as defined herein and $R^4$ is hydrogen or lower alkoxy comprises reacting the latter compound with 1.2 to 2 molar equivalents of a proton acceptor, preferably an inorganic base (i.e., sodium hydride, sodium methoxide, potassium t-butoxide and the like), in an inert solvent, selected from dimethylformamide and the like, at 10° to 50° C. for one to three hours. A di(lower)alkylamino(lower)alkyl chloride, bromide or iodide (1.2 to 2 molar equivalents) is added and the resulting mixture is stirred at 10° to 50° C. for 20 to 30 hours. Purification of the reaction mixture gives the corresponding compound of formula I in which $R^1$ is di(lower)alkylamino(lower)alkyl, $R^2$ and $R^3$ are as defined herein and $R^4$ is hydrogen or lower alkyl.

Alternatively, the latter compound and related compounds can be obtained by reacting the compound of formula I in which $R^1$ is hydrogen, $R^2$ and $R^3$ are as defined herein and $R^4$ is hydrogen or lower alkoxy with about two to four molar equivalents of an $\omega$-halo-alkanoyl halide wherein each of the halogen atoms is chlorine, bromine or iodine in the presence of a molar excess of a proton acceptor, preferably an organic base (i.e., triethylamine), in an inert organic solvent (i.e., methylene chloride or chloroform) at a temperature from 10° to 50° C for about 20 to 40 hours to obtain the corresponding $\omega$-halo-(lower)alkanoyl intermediate. Reaction of the latter intermediate with two to ten molar equivalents of ammonia, lower alkylamine equivalents of a proton acceptor, preferably an inorganic base selected from sodium or potassium hydroxide, in a lower alkanol (i.e., methanol, ethanol and the like) at about 10° to 40° C. for about 10 to 50 hours yields the corresponding amino, lower alkylamino or di(lower)-alkylamino alkanoyl intermediate. Reduction of the latter intermediate with a complex metal hydride, preferably lithium aluminum hydride in tetrahydrofuran, gives the corresponding compound of formula I in which $R^1$ is amino(lower)alkyl, lower alkylamino(lower)alkyl or di(lower)alkylamino(lower)alkyl, $R^2$ and $R^3$ are as defined herein and $R^4$ is hydrogen or lower alkoxy.

The compound of formula I in which $R^1$, $R^2$ and $R^3$ are as defined herein and $R^4$ is hydroxy is readily obtained by heating a mixture of the corresponding compound of formula I in which $R^1$, $R^2$ and $R^3$ are as defined herein and $R^4$ is lower alkoxy and pyridine hydrochloride at 150° to 200° C. for about two to four hours.

The following examples illustrate further this invention.

EXAMPLE 1

1-Methyl-3-phenyl-4-piperidinol; 11

Sodium borohydride (9.46 g) is added portionwise to a solution of the compound of formula IV, (-methyl-3-phenyl-4-piperidone (94.6 g, described by A. A. Patchett and F. F. Gianuso, supra), in water-methanol 1:9 (250 ml). The mixture is stirred for 30 minutes and the methanol is evaporated. The aqueous residue is diluted with water, 6N hydrochloric acid and washed with ether. The aqueous phase is made alkaline and extracted with chloroform. The chloroform extract is evaporated and crystallized from ether to give cis-1-methyl-3-phenyl-4-piperidinol, mp 131–133° C. Anhydrous hydrogen chloride is added to the mother liquors and the precipitate is crystallized from methanol-ether to give trans-1-methyl-3-phenyl-4-piperidnol hydrochloride, mp 131–133° C.

EXAMPLE 2

1-Methyl-3-(3-methoxyphenyl)-4-piperidinol; 11

By following the procedure of Example 1, 1-methyl-3-(3-methoxyphenyl)-4-piperidone (prepared according to procedure for 1-methyl-3-phenyl-4-piperidone as described by A. A. Patchett and F. F. Gianusso, supra) is reduced to obtain cis-1-methyl-3-(3-methoxyphenyl)-4-piperidinol, mp 141–143° C. and trans-1-methyl-3-(3-methoxyphenyl)-4 -piperidinol hydrobromide, mp 151–153° C.

In a similar manner but replacing 1-methyl-3-(3-methoxylphenyl)-4-piperidone with 1-butyl-3-phenyl-4-piperidone or 1-ethyl-3-(3-pentyloxyphenyl)-4-piperidinone, cis-1-butyl-3-phenyl-4-piperidone, trans-1-butyl-3-phenyl-4-piperidone, cis-1-ethyl-3-(3-pentyloxyphenyl)-4-piperidinol and trans-1-ethyl-3-(3-pentyloxyphenyl)-4-piperidinol are obtained.

EXAMPLE 3

(4a,10b-trans)-2,3,4,4a,6,10b-Hexahydro-2,6,6-trimethyl-1H-[2]-benzopyrano[4,3-c]pyridine; 1 ($R^1$, $R^2$ and $R^3$ = $CH_3$, and $R^4$ = H)

Anhydrous hydrogen bromide gas is bubbled into a solution of trans-1-methyl-3-phenyl-4-piperidinol (25 g, described in Example 1) in dioxane-acetone (9:1, 300 ml) at 0° C. for 80 hours. At 8 hour intervals, 50 ml of the dioxane-acetone mixture is added. The solution is filtered and evaporated. Water is added to the residue and the solution is washed with ether. The aqueous solution is made alkaline and extracted with ether. The organic extract is dried and maleic acid is added. The precipitate is crystallized from isopropanol to give the title compound as the maleate salt, mp 156–158° C.

In the same manner but replacing trans-1-methyl-3-phenyl-4-piperidinol with an equivalent amount of cis-1-methyl-3-phenyl-4-piperidinol (described in Example 1) or trans-1-butyl-3-phenyl-4- piperidinol (described in Example 2), (4a,10b-cis)-2,3,4,4a,6,10b-hexahydro-2,6,6-trimethyl-1H[2]benzopyrano[4,3-c]pyridine, HBr salt, mp 250–252° C. and (4a,10b-trans)-2,3,4,4a,6,10b-hexahydro-2-butyl-6,6-dimethyl-1H-[2]benzopyrano[4,3-c]pyridine are obtained respectively.

EXAMPLE 4

(4a,10b-trans)-2,3,4,4a,6,10b-Hexahydro-2-methyl-6-phenyl-1H-[2]benzopyrano[4,3-c]pyridine, 1 ($R^1$ = $CH_3$, $R^2$ and $R^4$ = H and $R^3$ = $C_6H_5$)

Hydrogen bromide gas is bubbled into a mixture at 0° C. of trans-1-3-phenyl-4-piperidinol (4.5 g, described in Example 1), molecular sieves (5g) and benzaldehyde (2.5 g) in methanol (100 ml) for 24 hours. Additional molecular sieves (5g) and benzaldehyde (2.5 g) are added and the hydrogen bromide addition is continued for an additional 24 hours. After filtering, the filtrate is diluted with ice-cold water and extracted with ether. The extract is evaporated and subjected to chromatography on silica gel using methanol-chloroform (1:4). The eluates are evaporated, dissolved in ether and treated with hydrogen bromide. The precipitate is crystallized from methanol to give the title compound as the HBr salt, mp > 300° C.

In the same manner but replacing benzaldehyde with an equivalent amount of propionaldehyde, S-trioxane, 3-pentanone or hexanal, the following compounds of formula I are obtained, (4a,10b-trans)-2,3,4,4a,6,10b-hexahydro-6-ethyl-2-methyl-1H-[2]benzopyrano[4,3-c]pyridine, HBr salt, mp 214–216° C., (4a,10b-trans)-2,3,4,4a,6,10b-hexahydro-2-methyl-1H-[2]benzopyrano[4,3-c]-pyridine, HBr salt, mp 202–204° C., (4a,10b-trans)-2,3,4,4a,6, -10b-hexahydro-6,6-diethyl-2-methyl-1H-[2]benzopyrano[4,3-c]-pyridine and (4a,10b-trans)-2,3,4,4a,6,10b-hexahydro-2-methyl-6-pentyl-1H-[2]benzopyrano[4,3-c]pyridine.

In a similar manner but replacing trans-1-methyl-3-phenyl-4-piperidinol with an equivalent amount of cis-1-methyl-3-phenyl-4-piperidinol (described in Example 1) or trans-1-butyl-3-phenyl-4-piperidinol (described in Example 2) and using benzaldehyde, (4a,10b-cis)-2,3,4,4a,6,10b-hexahydro-2-methyl-6-phenyl-1H-[2]benzopyrano[4,3-c]pyridine, HBr salt, mp 290–293° C., and (4a,10b-trans)-2,3,4,4a,6,10b-hexahydro-2-butyl-6-phenyl-1H-[2]benzopyrano[4,3-c]pyridine are obtained respectively.

EXAMPLE 5

(4a,10b-trans)-2,3,4,4a,6,10b-Hexahydro-9-methoxy-2,6,6-trimethyl-1H-[2]benzopyrano[4,3-c]pyridine; 1 ($R^1$, $R^2$ and $R^3$ = $CH_3$ and $R^4$ = $OCH_3$)

Hydrogen chloride gas is bubbled into a solution at 0° C. of trans-1-methyl-3-(3-methoxyphenyl)-4-piperidinol (4.4 g, described in Example 2) in dioxane-acetone (9:1, 100 ml) for one hour. The solution is evaporated, water is added and the solution is washed with ether. The aqueous phase is made alkaline and extracted wth ether. Maleic acid is added to the ether extract and the precipitate is crystallized from methanol to give the title compound as the maleate salt, mp 201–203° C.

In the same manner but replacing trans-1-methyl-3-(3-methoxyphenyl)-4-piperidinol with an equivalent amount of cis-1-methyl-3-(3-methoxyphenyl)-4-piperidinol (described in Example 2) or trans-1-ethyl-3-(3-pentyloxyphenyl)-4-piperidinol (described in Example 2), (4a,10b-cis)-2,3,4,4a,6,10b-hexahydro-9-methoxy-2,-6,6-trimethyl-1H-[2]benzopyrano[4,3-c]pyridine, HCl salt, mp 283–285° C., and (4a,10b-trans)2,3,4,4a,6,10b-hexahydro-9-pentyloxy-2-ethyl-6,6-dimethyl-1H[2]benzopyrano[4,3-c]pyridine are obtained respectively.

In the same manner but replacing acetone with an equivalent amount of 4-heptanone or pentanal, (4a,10b-trans)-2,3,4,4a,6,10b-hexahydro-9-methoxy-2-methyl-6,6-dipropyl-1H-[2]benzopyrano[4,3-c]pyridine and (4a,b 10b-trans-2,3,4,4a,6,10b-hexahydro-6-butyl-9-methoxy-2-methyl-1H[2]benzopyrano[4,3-c]pyridine are obtained respectively.

EXAMPLE 6

(4a,10b-trans)-2,3,4,4a,6,10b-Hexahydro-2,6-dimethyl-1H-[2]-benzopyrano[4,3-c]pyridine; 1 ($R^1$ and $R^2$ = $CH_3$ and $R^3$ and $R^4$ = H)

Hydrogen bromide gas is bubbled through a mixture at 0° C. of trans-1-methyl-3-phenyl-4-piperidinol (2.5 g, described in Example 1), paraldehyde (3 g), molecular sieves (5 g) and methanol (80 ml) for 3 days. After filtering, the solution is poured on ice, neutralized with saturated aqueous potassium cabonate and extracted with ether. The ether extract is evaporated and subjected to chromatography on silica gel using methanol-chloroform 1:4. The eluates are evaporated, dissolved in ether and treated with hydrogen bromide. The precipitate is crystallized from isopropanol to give the title compound as the HBr salt, mp 235°–239° C.

In the same manner but replacing trans-1-methyl-3-phenyl-4-piperidinol with an equivalent amount of trans-1-methyl-3-(3-methoxyphenyl)-4-piperidinol (described in Example 2) or cis-1-ethyl-3-(3-pentyloxyphenyl)-4-piperidinol (described in Example 2), (4a,10b-trans)-2,3,4,4a,6,10b-hexahydro-9-methoxy-2,6-dimethyl-1H-[2]benzopyrano[4,3-c]pyridine, HBr salt, mp 224°–226° C., and (4a,10b-cis)-2,3,4,4a,6,10b-hexahydro-2-ethyl-6-methyl-9-pentyloxy-1H-[2]-benzopyrano[4,3-c]pyridine are obtained respectively.

EXAMPLE 7

(4a,10b-trans)-2,3,4,4a,6,10b-hexahydro-9-methoxy-2-methyl-1H-[2]benzopyrano[4,3-c]pyridine; 1 ($R^1$ = $CH_3$, $R^2$ and $R^3$ = H and $R^4$ = $OCH_3$)

S-Trioxane (8 g) is added to a solution of trans-1-methyl-3-(3-methoxyphenyl)-4-piperidinol (7 g, described in Example 2) in dioxane (20 ml) followed by boron trifluoride etherate (25 ml). The solution is stirred at room temperature for 24 hours and poured on ice. Potassium carbonate is added until the solution is neutral and the solution is extracted with ether. The ether extract is evaporated and subjected to chromatography on silica gel using methanol-chloroform (1:4). The eluates are evaporated, dissolved in ether and treated with hydrogen chloride. The precipitate is crystallized from methanol to give the title compound as the HCl salt, mp 241°–242° C.

In the same manner but replacing trans-1-methyl-3-(3-methoxyphenyl)-4-piperidinol with an equivalent amount of cis-1-methyl-3-phenyl-4-piperidinol (described in Example 1), (4a,10b-cis)-2,3,4,4a,6,10b-hexahydro-2-methyl-1H-[2]-benzopyrano-[4,3-c]pyridine, HCl salt, mp 224°–226° C., is obtained.

EXAMPLE 8

(4a,10b-trans)-2,3,4,4a,6,10b-Hexahydro-1H-[2]benzopyrano[4,3-c]-pyridine-2-carbonitrile; 1 ($R^1$ = CN and $R^2$, $R^3$ and $R^4$ = H)

A solution of (4a,10b-trans)-2,3,4,4a,6,10b-hexahydro-2-methyl-1H-[2]benzopyrano[4,3-c]pyridine (0.319 g, described in Example 4) and cyanogen bromide (0.20 g) in chloroform (20 ml) is heated at reflux for two hours. The solution is evaporated and water (5 ml) is added. The mixture is heated to reflux, cooled and extracted with chloroform. The extract is evaporated and subjected to chromatography on silica gel using ethyl acetate-chloroform (1:19). The eluates are evaporated and crystallized from ethyl acetate to give the title compound, mp 141°–144° C.

In the same manner but replacing (4a,10b-trans)-2,3,4,4a,6,10b-hexahydro-2-methyl-1H-[2]benzopyrano[4,3-c]pyridine with an equivalent amount of (4a,10b-cis)-2,3,4,4a,6,10b-hexahydro-2-methyl-1H-[2]benzopyrano[4,3-c]pyridine (described in Example 7) or (4a,10b-trans)-2,3,4,4a,6,10b-hexahydro-9-methoxy-2-methyl-1H-[2]benzopyrano[4,3-c]pyridine (described in Example 7), the following compounds of formula I are obtained, (4a,10b-cis)-2,3,4,4a,6,10b-hexahydro-1H-[2]benzopyrano[4,3-c]pyridine-2-carbonitrile, mp 131°–134° C., and (4a,10b-trans)-2,3,4,4a,6,10b-hexahydro-9-methoxy-1H-[2]benzopyrano[4,3-c]pyridine-2-carbonitrile.

EXAMPLE 9

(4a,10b-trans)-2,3,4,4a,6,10b-Hexahydro-1H-[2]benzopyrano-[4,3-c]pyridine; 1 ($R^1$, $R^2$, $R^3$ and $R^4$ = H)

A solution of (4a,10b-trans)-2,3,4,4a,6,10b-hexahydro-1H-[2]benzopyrano[4,3-c]pyridine-2-carbonitrile (2.14 g, described in Example 8) in dry tetrahydrofuran (100 ml) is slowly added to a suspension of lithium aluminum hydride (1.5 g) in tetrahydrofuran (150 ml). The mixture is heated at reflux for 3 hours under nitrogen. Saturated aqueous potassium sodium tartrate (35 ml) is added and the mixture is extracted with chloroform. The chloroform extract is evaporated, dissolved in ether and treated with hydrogen chloride. The precipitate is crystallized from ethanol to give the title compound as the HCl salt, mp 219°–222° C.

In the same manner but replacing the above carbonitrile with the other 2-carbonitriles described in Example 8, the following compounds of formula I are obtained, (4a,10b-cis)-2,3,4,4a,6,10b-hexahydro-1H-[2]benzopyrano[4,3-c]pyridine, HCl salt, mp 190° C., and (4a,10b-trans)-2,3,4,4a,6,10b-hexahydro-9-methoxy-1H-[2]benzopyrano[4,3-c]pyridine.

EXAMPLE 10

(4a,10b-trans)-2,3,4,4a,6,10b-Hexahydro-9-methoxy-6,6-dimethyl-1H-[2]benzopyrano[4,3-c]pyridine; 1 ($R^1$ = H, $R^2$ and $R^3$ = $CH_3$ and $R^4$ = $OCH_3$)

A mixture of (4a,10b-trans)-2,3,4,4a,6,10b-hexahydro-9-methoxy-2,6,6-trimethyl-1H-[2]benzopyrano[4,3-c]pyridine (6.0 g, described in Example 5) and phenyl chloroformate (12 g) in toluene (75 ml) is heated at reflux for 8 hours. The solvent is evaporated and the residue is subjected to chromatography on silica gel using ethyl acetate-chloroform 1:9. The eluates are evaporated to give (4a,10b-trans)-2,3,4,4a,6,10b-hexahydro-9-methoxy-6,6-dimethyl-1H-[2]benzopyrano[2-]pyridine-2-carboxylic acid phenyl ester.

The latter compound (6.0 g) is heated to 130° C. and powdered potassium hydroxide (6 g) is added. The mixture is heated at 130° C. for one hour, dissolved in ethanol-water (1:1, 50 ml) and heated at reflux for two days. Water is added and the solution is extracted with ether. The ether extract is evaporated, dissolved in ether and treated with hydrogen chloride. The precipitate is crystallized from methanol to give the title compound as the HCl salt, mp 259°–260° C.

EXAMPLE 11

(4a,10b-trans)-2,3,4,4a,6,10b-Hexahydro-1H-[2]benzopyrano[4,3-c]-pyridine-2-carboximidamide; 1 ($R^1$ = C(=NH)NH$_2$ and $R^2$, $R^3$ and $R^4$ = H)

A solution of S-methylpseudothiourea (1.40 g) in isopropanol-water (1:1, 25 ml) is added to a solution of (4a,10b-trans)-2,3,4,4a,6,10b-hexahydro-1H-[2]benzopyrano-[4,3-c]pyridine (1.89 g, described in Example 9) in isopropanol-water (1:1, 25 ml). A solution of potassium carbonate (1.38 g) in water (5 ml) is added and the resulting mixture is heated at reflux overnight. The mixture is evaporated, dissolved in water and filtered. A solution of hydrogen bromide in methanol is added to the filtrate and the resulting precipitate is crystallized from water to give the title compound as the HBr salt, mp 304°–306° C.

EXAMPLE 12

(4a,10b-trans)-2,3,4,4a,6,10b-Hexahydro-2-ethyl-1H-[2]-benzopyrano[4,3-c]pyridine; 1 ($R^1$ = C$_2$H$_5$ and $R^2$, $R^3$ and $R^4$ = H)

A solution of 30% sodium hydroxide (20 ml) is added to a solution at 0° C. of (4a,10b-trans)-2,3,4,4a,6,10b-hexahydro-1H-[2]benzopyrano[4,3-c]pyridine (1.8 g described in Example 9) in methylene chloride (30 ml). Acetyl chloride (0.9 g) in methylene chloride (5 ml) is added dropwise. The organic phase is separated, washed with water, dried (MgSO$_4$), evaporated and crystallized from cyclohexane to obtain (4a,10b-trans)-2,3,4,4a,6,10b-hexahydro-2-acetyl-1H-[2]benzopyrano[4,3c]pyridine, mp 127° C.

A solution of the latter compound (2.45 g) in dry tetrahydrofuran (30 ml) is slowly added to a suspension of lithium aluminum hydride (0.6 g) in tetrahydrofuran (70 ml). The mixture is heated at reflux for one hour, cooled, treated with water and filtered. The filtrate is evaporated, dissolved in ether and treated with hydrogen bromide. The precipitate is crystallized from ethanol to give the title compound as the HBr salt, mp 256°–257° C.

In the same manner but replacing acetyl chloride with an equivalent amount of phenylacetyl chloride, cyclopropylcarbonyl chloride or propionyl chloride, the following compounds of formula I are obtained respectively: (4a,10b-trans)-2,3,4,4a,6,10b-hexahydro-2-(2-phenylethyl)-1H-[2]benzopyrano[4,3-c]pyridine, HBr salt, mp 256°–258° C.; (4a,10b-trans)-2,3,4,4a,6,10b-hexahydro-2-cyclopropylmethyl-1H-[2]benzopyrano[4,3-c]pyridine, HBr salt, mp 240°–241° C.; and (4a,10b-trans)-2,3,4,4a,6,10b-hexahydro-2-propyl-1H-[2]benzopyrano[4,3-c]pyridine, HBr salt, mp 255°–258° C.

In the same manner but replacing (4a,10b-trans)-2,3,4,4a,6,10b-hexahydro-1H-[2]benzopyrano[4,3-c]pyridine with an equivalent amount of (4a,10b-trans)-2,3,4,4a,6,10b-hexahydro-9-methoxy-1H-[2]benzopyrano[4,3-c]pyridine (described in Example 9), and using acetyl chloride or propionyl chloride, the following compounds of formula I are obtained: (4a,10b-trans)-2,3,4,4a,6,10b-hexahydro-2-ethyl-9-methoxy-1H-[2]benzopyrano[4,3-c]-pyridine, HBr salt, mp 252°–254° C., and (4a,10b-trans)-2,3,4,4a,6,10b-hexahydro-9-methoxy-2-propyl-1H-[2]benzopyrano[4,3-c]pyridine, HBr salt, mp 224°–226° C.

EXAMPLE 13

(4a,10b-trans)-2,3,4,4a,6,10b-Hexahydro-2-butyl-1H-[2]benzopyrano[4,3-c]pyridine; 1 ($R^1$ = C$_4$H$_9$ and $R^2$, $R^3$, and $R^4$ = H)

Butyric anhydride (3 ml) is added to a solution of (4a,10b-trans)-2,3,4,4a,6,10b-hexahydro-1H-[2]benzopyrano-[4,3-c]pyridine (3.0 g, described in Example 9) and triethylamine (3 ml) in dichloroethane (50 ml). The mixture is heated at reflux for 30 min., ice is added and the mixture is extracted with methylene chloride. The organic extract is washed with dilute hydrochloric acid, aqueous sodium carbonate, water, dried and evaporated. The residue is subjected to chromatography on silica gel using methanol-chloroform (1:9) followed by evaporation of the eluates to give (4a,10b-trans)-2,3,4,4a,6,10b-hexahydro-2-(1-oxobutyl)-1H-[2]benzopyrano[4,3-c]pyridine.

A solution of the latter compound (3.0 g) in dry tetrahydrofuran (100 ml) is slowly added to a suspension of lithium aluminum hydride (0.8 g) in tetrahydrofuran (40 ml). The mixture is heated at reflux for one hour, cooled, treated with water and filtered. The filtrate is evaporated, dissolved in ether, treated with hydrogen bromide and crystallized from ethanol to give the title compound as the HBr salt, mp 225°–227° C.

EXAMPLE 14

(4a,10b-trans)-2,3,4,4a,6,10b-Hexahydro-2-(2-propenyl)-1H-[2]benzopyrano[4,3-c]pyridine; 1 ($R^1$ = CH$_2$CH = CH$_2$ and $R^2$, $R^3$ and $R^4$ = H)

A mixture of (4a,10b-trans)-2,3,4,4a,6,10b-hexahydro-1H-[2]benzopyrano[4,3-c]pyridine (2.1 g, described in Example 9), 2-propenyl bromide (1.5 g) and potassium carbonate (1.8 g) in dioxane (50 ml) is stirred at room temperature for 48 hours. Water (50 ml) is added and the mixture extracted with ether. The ether extract is evaporated, dissolved in ether and treated with hydrogen bromide. The resulting precipitate is crystallized from methanol-ether to give the title compound as the HBr salt, mp 257°–259° C.

In the same manner but replacing 2-propenyl bromide with an equivalent amount of 2-bromopropane or 4-pentenyl bromide, (4a,10b-trans)-2,3,4,4a,6,10b-hexahydro-2-(1-methylethyl)-1H-[2]benzopyrano[4,3-c]pyridine, HBr salt, mp 268°–270° C., and (4a,10b-trans)-2,3,4,4a,6,10b-hexahydro-2-(4-pentenyl)-1H-[2]benzopyrano[4,3-c]pyridine are obtained respectively.

EXAMPLE 15

(4a,10b-trans)-2,3,4,4a,6,10b-Hexahydro-2-[2-(dimethylamino)-ethyl]-1H-[2]benzopyrano[4,3-c]pyridine; 1 ($R^1$ = (CH$_2$)$_2$N(CH$_3$)$_2$ and $R^2$, $R^3$ and $R^4$ = H)

A solution of (4a,10b-trans)-2,3,4,4a,6,10b-hexahydro-1H-[2]benzopyrano[4,3-c]pyridine (2 g, described in Example 9) in dry dimethylformamide (10 ml) is added dropwise to a stirred mixture of sodium hydride (1.50 g of 50% oil dispersion) in dimethylformamide (20 ml). The solution is stirred for two hours at room temperature. 2-Chloro-N,N-dimethylethylamine (2.3 g) is added and the mixture is stirred at room temperature overnight. The reaction mixture is poured into crushed ice, acidified with 6N hydrochloric acid, washed with ether, made alkaline and extracted with ether. The latter ether extract is dried over magnesium sulfate and evaporated. The residue is dissolved in ether and hydrogen bromide in ether is added. The precipitate is crystallized from ethanol to give the title compound as the HBr salt, mp 258°–260° C.

In the same manner but replacing 2-chloro-N,N-dimethylethylamine with an equivalent amount of 2-chloro-N,N-dipropylethylamine or 4-chloro-N,N-diethylbutylamine, (4a,10b-trans)-2,3,4,4a,6,10b-hexahydro-2-[2-(dipropylamino)ethyl]-1H-[2]benzopyrano[4,3-c]pyridine and (4a,10b-trans)-2,3,4,4a,6,10b-hexahydro-2-[4-(diethylamino)butyl]-1H-[2]benzopyrano[4,3-c]-pyridine are obtained respectively.

EXAMPLE 16

(4a,10b-trans)-2,3,4,4a,6,10b-Hexahydro-9-hydroxy-2,6,6-trimethyl-1H-[2]benzopyrano[4,3-c]pyridine; 1 ($R^1$, $R^2$ and $R^3$ = H and $R^4$ = OH)

A mixture of (4a,10b-trans)-2,3,4,4a,6,10b-hexahydro-9-methoxy-2,6,6-trimethyl-1H-[2]benzopyrano[4,3-c]pyridine (1.0 g, described in Example 5) and pyridine hydrochloride (5 g) is heated at 180° C. for three hours. The product is subjected to chromatography on silica gel using methanol-chloroform (1:4) and the eluates are evaporated. The residue is dissolved in ether and treated with hydrogen chloride. The precipitate is crystallized from methanol-ether to give the title compound as the HCl salt, mp 288°–291° C.

We claim:
1. (4a,10b-trans)-2,3,4,4a,6,10b-Hexahydro-2,6,6-trimethyl-1H-[2]benzopyrano[4,3-c]pyridine.
2. (4a,10b-cis)-2,3,4,4a,6,10b-Hexahydro-2,6,6-trimethyl-1H-[2]benzopyrano[4,3-c]pyridine.
3. (4a,10b-trans)-2,3,4,4a,6,10b-Hexahydro-2-methyl-6-phenyl-1H-[2]benzopyrano[4,3-c]pyridine.
4. (4a,10b-trans)-2,3,4,4a,6,10b-Hexahydro-2-methyl-1H-[2]benzopyrano[4,3-c]pyridine.
5. (4a,10b-trans)-2,3,4,4a,6,10b-Hexahydro-9-methoxy-2,6,6-trimethyl-1H-[2]benzopyrano[4,3-c]pyridine.
6. (4a,10b-cis)-2,3,4,4a,6,10b-Hexahydro-9-methoxy-2,6,6-trimethyl-1H-[2]benzopyrano[4,3-c]pyridine.
7. (4a,10b-trans)-2,3,4,4a,6,10b-Hexahydro-2,6-dimethyl-1H-[2]benzopyrano[4,3-c]pyridine.
8. (4a,10b-trans)-2,3,4,4a,6,10b-Hexahydro-9-methoxy-2,6-dimethyl-1H-[2]benzopyrano[4,3-c]pyridine.
9. (4a,10b-trans)-2,3,4,4a,6,10b-Hexahydro-9-methoxy-2-methyl-1H-[2]benzopyrano[4,3-c]pyridine.
10. (4a,10b-trans)-2,3,4,4a,6,10b-Hexahydro-1H-[2]benzopyrano[4,3-c]pyridine-2-carbonitrile.
11. (4a,10b-trans)-2,3,4,4a,6,10b-Hexahydro-1H-[2]benzopyrano[4,3-c]pyridine.
12. (4a,10b-trans)-2,3,4,4a,6,10b-Hexahydro-9-methoxy-6,6-dimethyl-1H-[2]benzopyrano[4,3-c]pyridine.
13. (4a,10b-trans)-2,3,4,4a,6,10b-Hexahydro-1H-[2]benzopyrano[4,3-c]pyridine-2-carboximidamide.
14. (4a,10b-trans)-2,3,4,4a,6,10b-Hexahydro-2-ethyl-1H-[2]benzopyrano[4,3-c]pyridine.
15. (4a,10b-trans)-2,3,4,4a,6,10b-Hexahydro-2-(2-phenylethyl)-1H-[2]benzopyrano[4,3-c]pyridine.
16. (4a,10b-trans)-2,3,4,4a,6,10b-Hexahydro-2-cyclopropylmethyl-1H-[2]benzopyrano[4,3-c]pyridine.
17. (4a,10b-trans)-2,3,4,4a,6,10b-Hexahydro-2-propyl-1H-[2]benzopyrano[4,3-c]pyridine.
18. (4a,10b-trans)-2,3,4,4a,6,10b-Hexahydro-2-ethyl-9-methoxy-1H-[2]benzopyrano[4,3-c]pyridine.
19. (4a,10b-trans)-2,3,4,4a,6,10b-Hexahydro-9-methoxy-2-propyl-1H-[2]benzopyrano[4,3-c]pyridine.
20. (4a,10b-trans)-2,3,4,4a,6,10b-Hexahydro-2-butyl-1H-[2]benzopyrano[4,3-c]pyridine.
21. (4a,10b-trans)-2,3,4,4a,6,10b-Hexahydro-2-(2-propenyl)-1H-[2]benzopyrano[4,3-c]pyridine.
22. (4a,10b-trans)-2,3,4,4a,6,10b-Hexahydro-2-(1-methylethyl)-1H-[2]benzopyrano[4,3-c]pyridine.
23. (4a,10b-trans)-2,3,4,4a,6,10b-Hexahydro-2-[2-(dimethylamino)ethyl]-1H-[2]benzopyrano[4,3-c]pyridine.
24. The process for preparing a compound of formula I

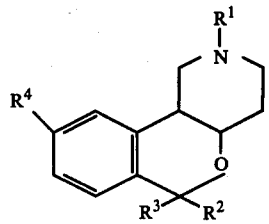

in which $R^1$ is hydrogen, lower alkyl, lower alkenyl, phenyl(lower)alkyl, lower cycloalkyl(lower)alkyl, aminoiminomethyl, cyano, amino(lower)alkyl, lower alkylamino(lower)alkyl or di(lower)alkylamino(lower)alkyl; $R^2$ is hydrogen or lower alkyl; $R^3$ is hydrogen, lower alkyl or phenyl; and $R^4$ is hydrogen, lower alkoxy or hydroxy; or a therapeutically acceptable acid addition salt thereof comprising
condensing a compound of formula II

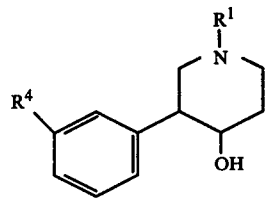

in which $R^1$ is lower alkyl and $R^4$ is hydrogen or lower alkoxy with a carbonyl compound of formula III.

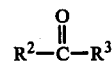

in which $R^2$ is hydrogen or lower alkyl and $R^3$ is hydrogen, lower alkyl or phenyl in the presence of an acid catalyst to obtain the corresponding compound of formula I in which $R^1$ is lower alkyl, $R^2$ is hydrogen or lower alkyl, $R^3$ is hydrogen, lower alkyl or phenyl and $R^4$ is hydrogen or lower alkoxy; and if desired,
(a) reacting said compound of formula I in which $R^1$ is methyl, $R^2$ and $R^3$ are as defined herein and $R^4$ is hydrogen or lower alkoxy with cyanogen bromide to obtain the corresponding compound of formula I in which $R^1$ is cyano and $R^2$, $R^3$ and $R^4$ are as defined immediately above; or
(b) reducing said last-named compound of formula I with a complex metal hydride to obtain the corresponding compound of formula I in which $R^1$ is hydrogen and $R^2$, $R^3$ and $R^4$ are as defined immediately above; or
(c) reacting said compound of formula I in which $R^1$ is methyl and $R^2$, $R^3$ and $R^4$ are as defined immediately above with phenyl chloroformate followed by heating with powdered sodium or potassium hydroxide to obtain the corresponding compound of formula I in which $R^1$ is hydrogen and $R^2$, $R^3$ and $R^4$ are as defined immediately above; or (d) reacting said last-named compound of formula I with S-methylpseudothiourea to obtain the corresponding compound of formula I in which $R^1$ is aminoiminomethyl and $R^2$, $R^3$ and $R^4$ are as defined immediately above; or (e) reacting said compound of formula I in which $R^1$ is hydrogen and $R^2$, $R^3$ and $R^4$ are as defined immediately above with a lower cycloalkylcarbonyl halide, lower alkanoyl halide, lower cycloalkyl(lower)alkanoyl halide, phenyl(lower)alkanoyl halide or benzoyl halide wherein the halide is chlorine, bromine or iodine followed by reduction of the corresponding amide, so obtained, with a complex metal hydride to obtain the corresponding compound of formula I in which $R^1$ is lower alkyl, lower cycloalkyl(lower)alkyl or phenyl(lower)alkyl and $R^2$, $R^3$ and $R^4$ are as defined immediately above; or (f) reacting said compound of formula I in which $R^1$ is hydrogen and $R^2$, $R^3$ and $R^4$ are as defined immediately above with a lower alkyl halide, lower cycloalkyl(lower)alkyl halide or lower alkenyl halide wherein the halide is bromide, chloride or iodide to obtain the corresponding compound of formula I in which $R^1$ is lower alkyl, lower cycloalkyl(lower)alkyl or lower alkenyl and $R^2$, $R^3$ and $R^4$ are as defined immediately above; or (g) reacting said compound of formula I in which $R^1$ is hydrogen and $R^2$, $R^3$ and $R^4$ are as defined immediately above with a proton acceptor followed by a di(lower)alkylamino(lower)alkyl chloride, bromide or iodide to obtain the corresponding compound of formula I in which $R^1$ is di(lower)alkylamino(lower)alkyl and $R^2$, $R^3$ and $R^4$ are as defined immediately above; or (h) reacting said compound of formula I in which $R^1$ is hydrogen and $R^2$, $R^3$ and $R^4$ are as defined immediately above with an $\omega$-halo-alkanoyl halide wherein each of the halogen atoms is chlorine, bromine or iodine in the presence of an organic proton acceptor to obtain the corresponding $\omega$-halo(lower)alkanoyl intermediate, reacting the latter intermediate with ammonia, lower alkylamine or di(lower)alkylamine in the presence of an inorganic proton acceptor to obtain the corresponding amino, lower alkylamino or di(lower)alkylamino alkanoyl intermediate and reducing the latter intermediate with a complex metal hydride to obtain the corresponding compound of formula I in which $R^1$ is amino(lower)alkyl, lower alkylamino(lower)alkyl or di(lower)alkylamino(lower)alkyl; $R^2$ and $R^3$ are as defined herein and $R^4$ is hydrogen or lower alkoxy; or (i) heating said compound of formula I in which $R^1$, $R^2$ and $R^3$ are as defined herein and $R^4$ is lower alkoxy with pyridine hydrochloride to obtain the corresponding compound of formula I in which $R^1$, $R^2$ and $R^3$ are as defined herein and $R^4$ is hydroxy.

* * * * *